United States Patent
Arbesman et al.

(10) Patent No.: US 8,742,196 B2
(45) Date of Patent: Jun. 3, 2014

(54) PRECUT ADHESIVE BODY SUPPORT ARTICLES AND SUPPORT SYSTEM

(76) Inventors: Ray Arbesman, Toronto (CA); Kevin Jardine, Toronto (CA)

(*) Notice: Subject to any disclaimer, the term of this patent is extended or adjusted under 35 U.S.C. 154(b) by 478 days.

(21) Appl. No.: 12/526,829

(22) PCT Filed: Feb. 6, 2008

(86) PCT No.: PCT/CA2008/000233
§ 371 (c)(1),
(2), (4) Date: Sep. 25, 2009

(87) PCT Pub. No.: WO2008/101314
PCT Pub. Date: Aug. 28, 2008

(65) Prior Publication Data
US 2010/0016771 A1    Jan. 21, 2010

(30) Foreign Application Priority Data

Feb. 19, 2007    (CA) .................................... 2578927

(51) Int. Cl.
*A61F 13/00*    (2006.01)
*A61F 5/00*    (2006.01)

(52) U.S. Cl.
USPC .................. 602/54; 602/53; 602/57; 602/60; 602/61

(58) Field of Classification Search
USPC ..................... 602/41–59, 75–79, 5; D24/189; 128/888, 889
See application file for complete search history.

(56) References Cited

U.S. PATENT DOCUMENTS

| | | | |
|---|---|---|---|
| 2,310,082 A | | 2/1943 | Holbrooke |
| 2,321,363 A | * | 6/1943 | Crowley .................. 602/44 |
| 2,349,709 A | | 5/1944 | Evans |
| 2,399,545 A | | 4/1946 | Davis |
| 2,415,276 A | | 2/1947 | Buckley et al. |
| 2,508,855 A | | 5/1950 | Brown |
| 2,592,801 A | | 4/1952 | Hanington |

(Continued)

FOREIGN PATENT DOCUMENTS

| | | |
|---|---|---|
| EP | 1 716 829 | 11/2006 |
| JP | 54-49197 | 4/1979 |

(Continued)

OTHER PUBLICATIONS

Kinesio Tex Website, dated May 8, 2008, Retrieved from the Internet: <URL: http://www.kinesio-tape.com/KinesioTex1.html >, published 2007.

(Continued)

*Primary Examiner* — Kim M Lewis
(74) *Attorney, Agent, or Firm* — Patterson & Sheridan, L.L.P.

(57) ABSTRACT

The invention provides an adhesive support article for supporting a body part of a user. A single-sided stretchable adhesive tape blank is precut into a sheet having a central anchoring portion and a plurality of outwardly extending fingers. The sheet is marked with visual indicators to guide the user of the support article for applying the central anchoring portion onto a first exterior surface of the body part and for stretching the fingers before adhering them at a predetermined distance away from the central anchoring portion. The adhesive support article can also be provided in a support system with at least one corresponding body landmark article, providing further guidance for applying the support article to the desired body part.

7 Claims, 12 Drawing Sheets

(56) References Cited

U.S. PATENT DOCUMENTS

| | | | |
|---|---|---|---|
| 2,740,403 A | | 4/1956 | Schueler |
| 2,861,006 A | | 11/1958 | Salditt |
| 2,940,868 A | | 6/1960 | Patchell |
| 3,199,548 A | | 8/1965 | Conant |
| 3,529,597 A | * | 9/1970 | Fuzak .............................. 602/58 |
| 3,618,754 A | | 11/1971 | Hoey |
| 3,677,250 A | * | 7/1972 | Thomas ........................ 604/180 |
| 3,853,598 A | | 12/1974 | Raguse |
| 3,971,374 A | * | 7/1976 | Wagner ............................. 602/58 |
| 3,989,041 A | | 11/1976 | Davies |
| 4,207,885 A | | 6/1980 | Hampton et al. |
| 4,236,550 A | | 12/1980 | Braun et al. |
| 4,345,590 A | | 8/1982 | Nakajima |
| 4,424,808 A | | 1/1984 | Schafer et al. |
| 4,485,809 A | * | 12/1984 | Dellas .............................. 602/52 |
| 4,665,909 A | | 5/1987 | Trainor |
| 4,699,133 A | | 10/1987 | Schafer et al. |
| 4,702,948 A | | 10/1987 | Sieber-Gadient |
| 4,734,320 A | * | 3/1988 | Ohira et al. .................. 428/40.1 |
| 4,737,400 A | | 4/1988 | Edison et al. |
| 4,891,040 A | | 1/1990 | Nagai et al. |
| 5,047,285 A | | 9/1991 | Ward |
| 5,139,476 A | * | 8/1992 | Peters .............................. 602/26 |
| D330,255 S | * | 10/1992 | Nelson, Jr. .................... D24/189 |
| 5,279,891 A | | 1/1994 | Ward |
| 5,480,708 A | | 1/1996 | Cheng |
| 5,749,843 A | | 5/1998 | Miller |
| 5,795,834 A | | 8/1998 | Deeb et al. |
| 5,861,348 A | | 1/1999 | Kase |
| 6,048,806 A | | 4/2000 | Deeb et al. |
| 6,447,470 B2 | * | 9/2002 | Bodenschatz et al. .......... 602/75 |
| 6,455,752 B1 | * | 9/2002 | Vesey .............................. 602/41 |
| 6,512,158 B1 | * | 1/2003 | Dobos .............................. 602/41 |
| 6,849,057 B2 | | 2/2005 | Satou et al. |
| 7,419,476 B2 | | 9/2008 | Oohira et al. |
| 2008/0154169 A1 | | 6/2008 | Kase |

FOREIGN PATENT DOCUMENTS

| | | |
|---|---|---|
| JP | 61-39135 | 3/1986 |
| JP | 61-257644 | 11/1986 |
| JP | 63-135621 | 9/1988 |
| JP | 64-061534 | 3/1989 |
| JP | 64-040421 | 10/1989 |
| JP | 4-18512 | 2/1992 |
| JP | 4-110723 | 9/1992 |
| JP | 7-43330 | 8/1995 |
| JP | 08-112304 | 5/1996 |
| JP | 2000-245771 | 9/2000 |
| JP | 2001-000463 | 1/2001 |
| JP | 2001-104366 | 4/2001 |

OTHER PUBLICATIONS

International Search Report for International Application No. PCT/CA2008/000233, dated May 14, 2008.

Naoko Aminaka and Phillip A. Gribble, Patellar Taping, Patellofemoral Pain Syndrome, Lower Extremity Kinematics, and Dynamic Postural Control, Journal of Athletic Training, 2008, pp. 21-28, vol. 43(1).

Dariusz Bialoszewski, Weronika Wozniak, and Slawomir Zarek, Clinical Efficacy of Kinesiology Taping in Reducing Edema of the Lower Limbs in Patients Treated With the Ilizarov Method—Preliminary Report, Ortop Traumatol Rehabil, 2009, pp. 46-54, vol. 11.

A. M. Cools, E. E. Witvrouw, L. A. Danneels, and D. C. Cambier, Does Taping Influence Electromyographic Muscle Activity in the Scapular Rotators in Healthy Shoulders, Manual Therapy, 2002, pp. 154-162, vol. 7(3).

Tieh-Cheng Fu, Alice M. K. Wong, Yu-Cheng Pei, Katie P. Wu, Shih-Wei Chou, and Yin-Chou Lin, Effect of Kinesio Taping on Muscle Strength in Athletes—A Pilot Study, Journal of Science and Medicine in Sport, 2008, pp. 198-201, vol. 11.

J.M. Greve, J. D. Rossi, W. Cossermelli, and Filho Ferreira, Functional Rehabilitation of Degenerative Tendinous Injuries of the Shoulder, Rev. Hosp Clin Fac Med Sao Paulo, Mar.-Apr. 1991, vol. 46(2) (English Abstract submitted).

Yin-Hsin Hsu, Wen-Yin Chen, Hsiu-Chen Lin, Wendy T. J. Wang, and Yi-Fen Shih, The Effects of Taping on Scapular Kinematics and Muscle Performance in Baseball Players with Shoulder Impingement Syndrome, Journal of Electromyography and Kinesiology 19, 2009, pp. 1092-1099.

Ewa Jaraczewska and Carol Long, Kinesio Taping in Stroke: Improving Functional Use of the Upper Extremity in Hemiplegia, Topics in Stroke Rehabilitation, Summer 2006, pp. 31-42.

Kenzo Kase, Illustrated Kinesio Taping, Fourth Edition, Ken'l Kai Information, 2005.

Kenzo Kase, Jim Wallis, and Tsuyoshi Kase, Clinical Therapeutic Applications of the Kinesio Taping Method, $2^{nd}$ Edition, Tokyo: Kenzo Kase, 2003.

Kenzo Kase, Tasuyaki Hashimoto, and Tomoki Okane, Kinesio Taping Perfect Manual, 1996, Japan, Kinesio Taping Association.

Yuh-Hwan Liu, Shu-Min Chen, Chi-Yi Lin, Chung-I Huang, and Yung-Nien Sun, Motion Tracking on Elbow Tissue from Ultrasonic Image Sequence for Patients with Lateral Epicondylitis, Proceedings of the $29^{th}$ Annual International Conference of the IEEE EMBS, Lyon, France, Aug. 23-26, 2007, pp. 95-98.

Michael B. Miller, Iatrogenic and Nurisgenic Effects of Prolonged Immobilization of the III Aged, Journal of the American Geriatrics Society, Jul. 1975, vol. XXIII, No. 7, pp. 360-369.

S. O'Leary, M. Carroll, R. Mellor, A. Scott, and B. Vicenzino, The Effect of Soft Tissue Deloading on Thoracic Spine Pressure Pain Thresholds in Asymptomatic Subjects, Manual Therapy, 2002, pp. 150-153, vol. 7(3).

Steven B. Purcell, Brynn E. Schuckman, Carrie L. Docherty, John Schrader, and Wendy Poppy, Differences in Ankle Range of Motion Before and After Exercise in 2 Tape Conditions, The American Journal of Sports Medicine, 2009, pp. 383-389, vol. 37, No. 2.

David M. Selkowitz, Casey Chaney, Sandra J. Stuckey, and Georgeanne Vlad, The Effects of Scapular Taping on the Surface Electromyographia Signal Amplitude of Shoulder Girdle Muscles During Upper Extremity Elevation in Individuals With Suspected Shoulder Impingement Syndrome, Journal of Orthopaedic Sports Physical Therapy, Nov. 2007, vol. 37, No. 11.

Anna Slupik, Michael Dwornik, Dariusz Bialoszewski, and Emilia Zych, Effect of Kinesio Taping on Bioelectrical Activity of Vastus Medialis Muscle Preliminary Report, Ortop Traumatol Rehabil, Medsportpress, Nov.-Dec. 2007, pp. 644-651, vol. 9.

Mark D. Thelen, James A Dauber, and Paul D. Stoneman, The Clinical Efficacy of Kinesio Tape for Shoulder Pain: A Randomized, Double-Blinded, Clinical Trial, Journal of Orthopaedic & Sports Physical Therapy, Jul. 2008, pp. 389-395, vol. 38, No. 7.

Han-Ju Tsai, Hsiu-Chuan Hung, Jing-Lan Yang, Chiun-Sheng Huang, and Jau-Yih Tsauo, Could Kinesio Tape Replace the Bandage in Decongestive Lymphatic Therapy for Breast-Cancer-Related Lymphedema? A Pilot Study, Support Care Cancer, 2009, pp. 1353-1360.

Audrey Yasukawa, Payal Patel, and Charles Sisung, Pilot Study: Investigating the Effects of Kinesio Taping in an Acute Pediatric Rehabilitation Setting, The American Journal of Occupational Therapy, Jan./Feb. 2006, pp. 104-110, vol. 60, No. 1.

Ayako Yoshida and Leamor Kahanov, The Effect of Kinesio Taping on Lower Trunk Range of Motions, Research in Sports Medicine, 2007, pp. 103-112, vol. 15.

Canadian Office Action for Application No. 2,578,927 dated Jan. 19, 2011.

Akuta Co., Ltd., "Maestro Kojy's Words of Encouragement—Go Into Business!", New-Hale, Sep. 2006.

* cited by examiner

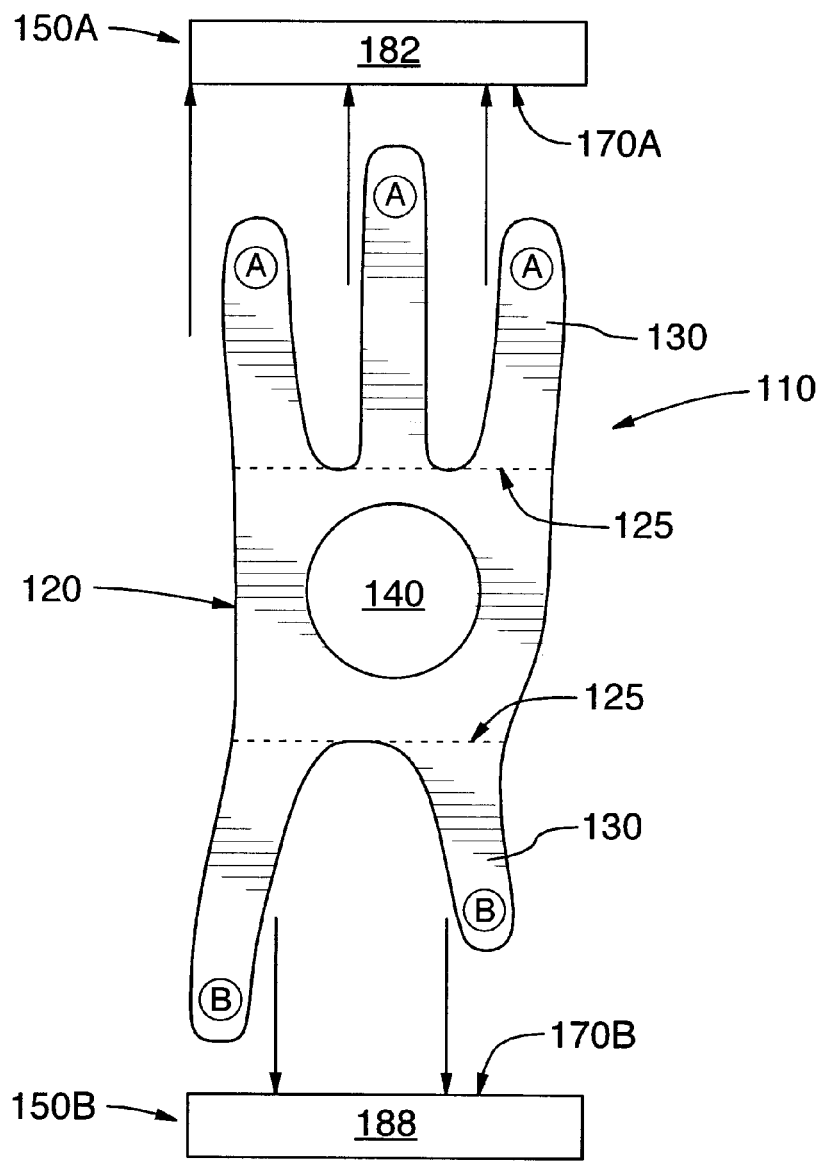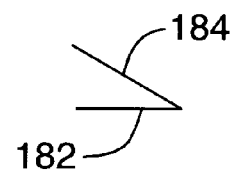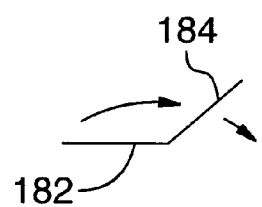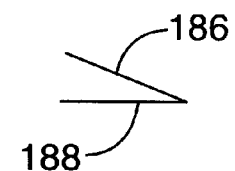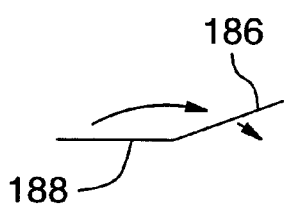
FIG.5
FIG.6
FIG.7
FIG.8
FIG.9

PRECUT ADHESIVE BODY SUPPORT ARTICLES AND SUPPORT SYSTEM

FIELD OF THE INVENTION

The invention relates to articles for supporting a user body part and more particularly to adhesive body support articles.

BACKGROUND OF THE INVENTION

A relatively new tool in the physiotherapy and sports medicine arsenal is high-stretch adhesive support tape. Such tape is distinct from traditional "sports" tape which is used to isolate and restrain a body part to protect it and allow healing. It is also distinct from traditional wrap bandages (e.g. TENSOR® bandages), which although stretchable, are primarily used for bracing an injury. High-stretch adhesive support tape, by contrast, is used for the purpose of positioning the body part (typically a joint) while permitting a high degree of natural mobility.

High-stretch adhesive support tape acts as an assist to weak musculature. The stretch in the tape allows a mild degree of tension to be placed across the supported body part, in effect acting as an auxiliary muscle.

High-stretch adhesive support tape can also be used for pain therapy in acute situations. The tape lifts the skin providing a stimulus to the fascia and/or muscular tissue, stimulates blood and lymphatic flow, alters the forces over the affected joint, effects muscle inhibition and facilitation, and stimulates muscle and skin receptors such as mechanoreceptors, nociceptors, exteroceptive receptors, and cutaneous proprioceptive afferents.

The adhesive aspect of the tape is critical to producing these effects. The tape sticks directly to the body. The adhesive is strong enough that opposite ends of a length of tape applied to the body will remain adhered even when the tape length is under tension and the body part is in regular active use. This contrasts with other tapes that are either non-adhesive or adhesive only to themselves. These tapes can be wrapped repeatedly on a body part or dispensed from a self-adhesive roll but cannot be adhered directly to the body.

One particularly effective type of high-stretch adhesive support tape is Kinesio Tex™ by Kinesio Co., Ltd. of Japan. This tape has many of the advantageous properties discussed above. However, it suffers several drawbacks, relating to the fact that it is sold in rolls, which must be customized for application according to the imagination and skill of the doctor. A physiotherapist or sports doctor must cut off a section of the tape from a roll, cut the length of tape further into a therapeutic shape, and apply it to the patient. The cutting, shaping and positioning (tensioning) of the tape piece are left to the complete discretion of the doctor. It is a trial and error process. The doctor is effectively trying to estimate a position, length, shape and degree of tension that will cause a subjective improvement in sensation, range of motion or pain relief in the patient.

The tape includes no visual indication of where or how to position it on the patient's body or how to use the stretch property effectively (what tension to apply). As a result, it is possible to position the tape incorrectly or with an inappropriate tension reducing the therapeutic effectiveness, reducing or constricting blood circulation, or even worsening the underlying condition.

For the patient, this trial and error process can be frustrating. Obtaining relief and/or satisfactory support from the tape is thus heavily dependent on the skill of the particular doctor and his/her experience with the tape product. Furthermore, the patient is committed to attending regularly at the doctor's office to have the tape freshly applied, since the tape is not typically available to patients directly, and in any case, could not be applied without considerable professional guidance.

For the doctor, the tape cutting and shaping are time-consuming and may be impossible to accommodate in a busy practice. Most doctors do not see their patients on a sufficiently regular basis to keep up a continuous tape therapy. There may be long gaps between "tape application" visits for chronic conditions, during which gaps the patient has no self-treatment option.

Another drawback of existing tapes is that they are frequently only available in narrower widths (less than 3 inches). While a narrow width provides a convenient size for packaging on a roll, the size is not conducive to effective coverage for support of many body parts. The doctor applying the tape may have to cut and apply multiple pieces of tape to achieve the desired effect. This complicates the application process and increases the time commitment.

It would be desirable to provide a pre-cut, pre-engineered adhesive body support article to overcome the aforementioned problems of high-stretch adhesive support tapes.

SUMMARY OF THE INVENTION

According to a first aspect of the invention, an adhesive support article is provided for supporting a body part of a user. A single-sided stretchable adhesive tape blank is precut into a sheet to form the adhesive support article. The sheet has a central anchoring portion and a plurality of fingers extending outwardly from the central anchoring portion. The sheet is marked with visual indicators to guide the user of the support article for:

applying the central anchoring portion onto a first exterior surface of the body part; and stretching the fingers a predetermined distance away from the central anchoring portion according to the marked indicators and adhesively applying the fingers to a second exterior surface of the body part spaced away from the first exterior surface to support the body part by tethering the first and second exterior surfaces together.

The tape blank preferably comprises a waterproof, breathable, high-elasticity physiotherapy tape.

The central anchoring portion may define a centrally positioned hole for allowing a joint to protrude through the sheet. This aids with positioning of the support article and enhances user comfort.

The fingers may be the same length or different lengths. The fingers may comprise alternating longer and shorter lengths. The length of the fingers is used to pre-calibrate the tension that will be present in the completely installed article. Shorter fingers will be stretched more than longer fingers. Longer fingers may be adhered with no tension at all.

Preferably, the central anchoring portion comprises a generally rectangular portion having two opposing longer sides and two opposing shorter sides. The fingers may extend outward from one or both of the two longer sides. The central anchoring portion defines an axis along its length. The fingers may extend at a perpendicular or non-perpendicular angle to the axis. In one embodiment, the fingers are precut to extend helically outward from the central anchoring portion.

To aid in installation, the sheet may comprise a release liner. The release liner is preferably scored to provide separate releasable portions at the central anchoring portion and at the fingers, so as to facilitate placement of the central anchoring portion before stretching and adhering the fingers.

The indicators on the sheet may comprise numerical indicators, letter indicators, or other indicators (such as pictograms or color codes). These may be marked on the fingers, the central anchoring portion or both. Preferably, a set of coordinating indicators are used on the fingers and the central anchoring portion to facilitate installation. The indictors may be marked to guide the user of the support article for overlapping the fingers when applying them.

In one embodiment of the support article, the central anchoring portion has a U shape with a pair of side portions joined by a base portion. The fingers extend from at least one of the side portions of the U. Each finger may extend from one of the side portions be stretchable toward the other side portion. The indicators may be marked to guide the user of the support article for stretching the fingers from one side portion to the other side portion when applying them. Alternatively, the indicators may be marked to guide the user of the support article for stretching the fingers toward the base portion when applying them.

According to a second aspect of the invention, an adhesive support system is provided. The system includes an adhesive support article and at least one adhesive body landmark article. The support article is adapted for supporting a body part of a user and comprises:
  a single-sided stretchable adhesive tape blank precut into a sheet having a central anchoring portion and a plurality of fingers extending outwardly from the central anchoring portion.

The sheet is marked with visual indicators to guide the user of the support article for:
  applying the central anchoring portion onto a first exterior surface of the body part; and
  stretching the fingers a predetermined distance away from the central anchoring portion according to the marked indicators and adhesively applying the fingers to a second exterior surface of the body part spaced away from the first exterior surface to support the body part by tethering the first and second exterior surfaces together.

The at least one adhesive body landmark article is adapted for adhering to an identifiable body landmark of the user to aid in gauging how far to stretch the fingers of the support article to adhere the fingers to the second exterior surface according to the marked indicators. The body landmark article may, for instance, be manufactured to a length that corresponds to the distance the fingers should be stretched from the central anchoring portion.

Preferably, the body landmark article is marked with a second set of indicators corresponding to the indicators on the support article.

Preferably, the system is packaged with instructions for the order of application of the body landmark article and the support article. It may be desirable to apply the body landmark article before the support article, or after.

The body landmark article is preferably pre-folded into halves at a central fold line. The body landmark article preferably includes a release liner, which is also scored at the central fold line to permit the pre-folded halves to be adhered separately. Preferably, at least one of the halves of the body landmark article is adapted to overlap and retain at least a portion of the fingers of the body support article when the fingers are adhered in the indicated position. The overlapping half of the body landmark article may be marked with indicators corresponding to indicators on the fingers that it overlaps.

According to a third aspect of the invention, a further adhesive support article is provided for supporting a body part of a user. The article combines a support article similar to the first embodiment with body landmarks similar to the second embodiment. The embodiment differs in that the support article and body landmarks are integral with each other in one unified support article. A single-sided stretchable adhesive tape blank precut into a sheet has:
  a central anchoring portion;
  a plurality of fingers extending outwardly from the central anchoring portion;
  at least one T-shaped body landmark projection extending outwardly from the central anchoring portion beyond the fingers, the body landmark having a pair of laterally extending wing members.

The sheet is marked on the fingers and the at least one body landmark with visual indicators to guide the user of the support article for:
  applying the central anchoring portion onto a first exterior surface of the body part;
  applying the at least one body landmark onto a second exterior surface of the body part; and
  stretching the fingers away from the central anchoring portion to meet the wing members of the body landmark before adhesively applying the fingers, to thereby support the body part by tethering the first and second exterior surfaces together.

The invention has numerous advantages over the prior art. The support article and support system provide improved user-friendly adhesive support over existing tapes requiring professional cutting and shaping. The invention also provides an objectively engineered design which eliminates the guesswork of the prior tape systems, allowing tension to be pre-calibrated so that users can apply the articles themselves, providing an effective self management strategy for those suffering from painful joints and/or chronic weakness.

The pre-cut shape of the support article further allows for a physiologically more effective adhesive support for supporting a joint, as all of the extensions (fingers) of the support article are focused around an anatomically significant central point allowing the central anchoring portion and fingers to work together increasing the overall effectiveness. The single piece (or single piece with body landmarks) design provides continuous support to work in an interdependent manner providing muscular facilitation and inhibition as well as cutaneous proprioceptive input.

Physiologically, the support article is designed to pull the cutaneous attachment of the support, the projections (fingers) back toward the central anchoring portion relieving tension on the underlying superficial fascia and providing afferent sensory input altering pain reception and joint awareness. This is believed to closely replicate how the human body work by means of a continuous interfacing of fascia. Skin irritation from friction is minimized as the adhesive support and the underlying skin move as one unit.

Unlike wrap bandages and other forms of braces (both adhesive and non-adhesive), this form of support does not restrict expansion of the muscles or compression of subcutaneous blood flow and is therefore safer for application by unskilled users.

A further advantage of the support system is that the body landmarks can be used to provide additional stabilization of the fingers of the support article. In an overlapping configuration, the landmarks overlap the finger "tips" thereby preventing curling and premature delamination of the fingers when in use.

BRIEF DESCRIPTION OF THE FIGURES

FIG. 5 shows a top plan view of a first stage of installation of a body support system having a body support article and upper and lower body landmark articles.

FIG. 6 shows a side view of the upper body landmark article folded prior to installation.

FIG. 7 shows a side view of the upper body landmark article being unfolded in the course of first stage installation.

FIG. 8 shows a side view of the lower body landmark article folded prior to installation.

FIG. 9 shows a side view of the lower body landmark article being unfolded in the course of first stage installation.

DETAILED DESCRIPTION

Figure 1:
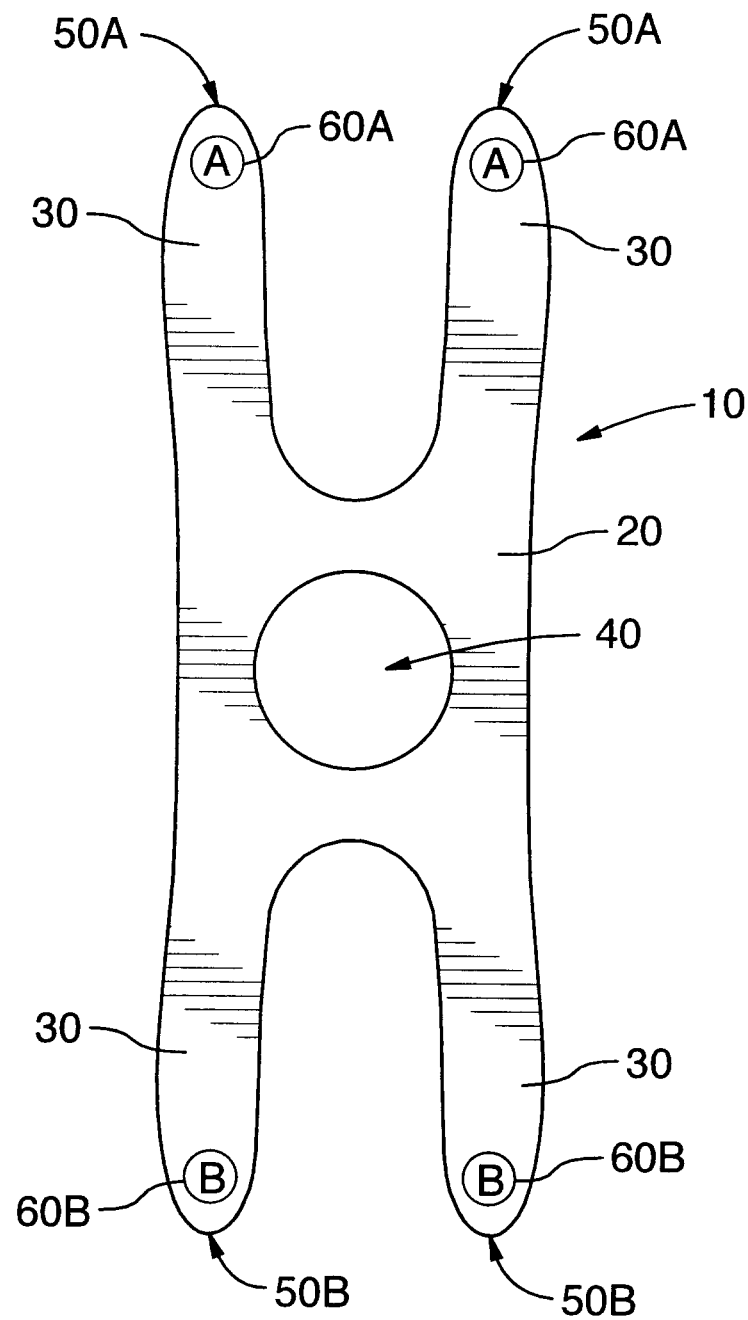
FIG. 1 shows a top plan view of a first body support article according to the present invention.
Figure 2:
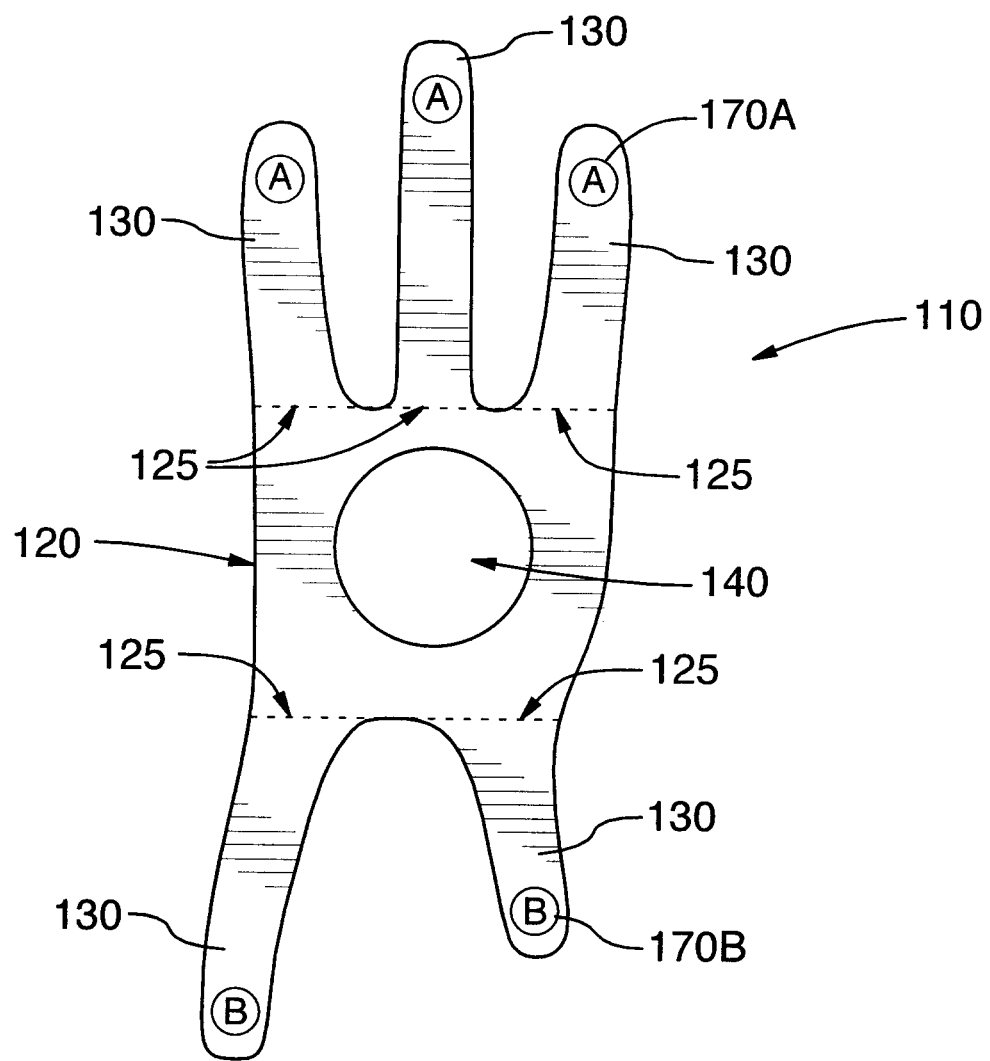
FIG. 2 shows a top plan view of a second body support article according to the present invention.
Figure 13:
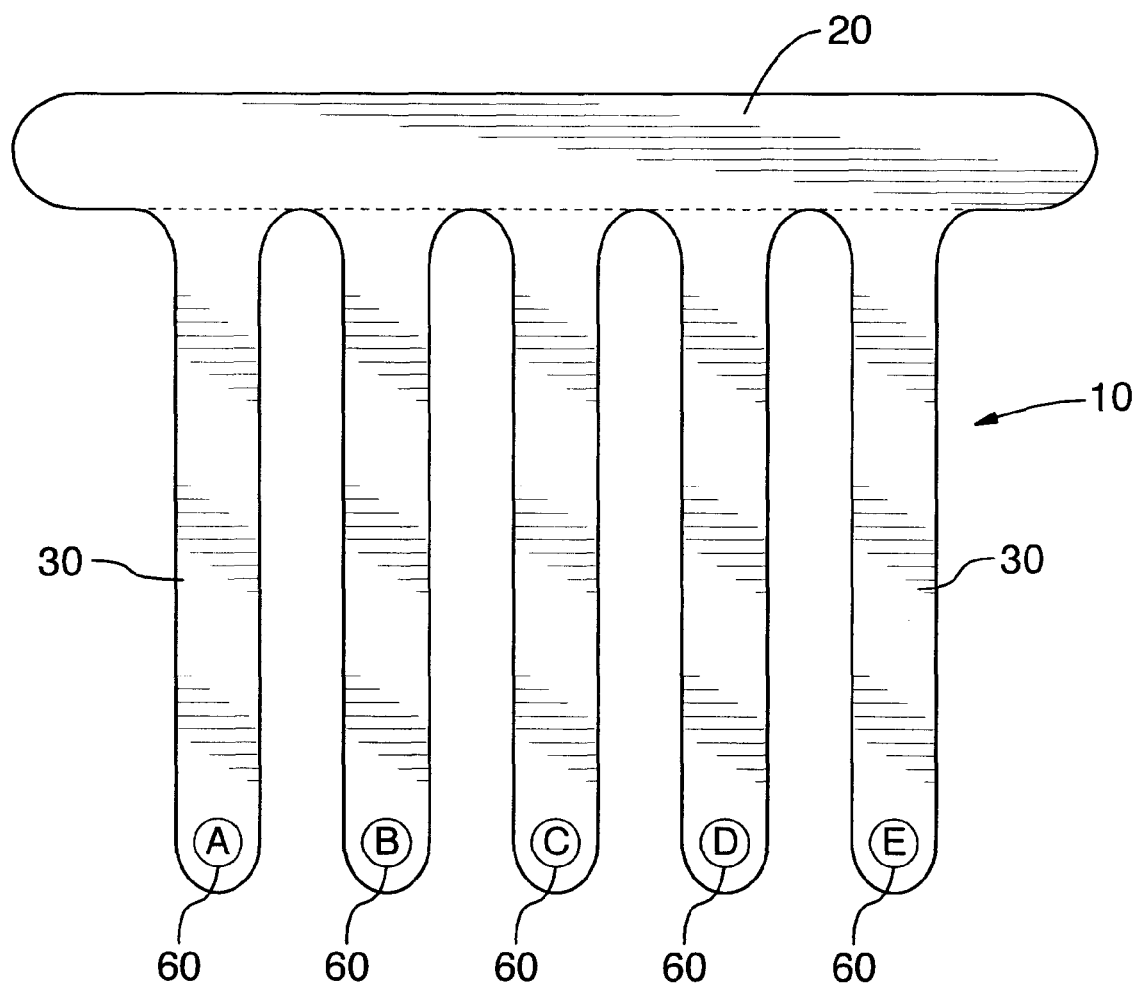
FIG. 13 shows a top plan view of a variation of the first body support article, having fingers extending in one direction only.

FIG. 1 illustrates a very simplistic adhesive body support 10 according to the present invention. For the greatest simplicity, a single fixed shape may be used which is capable of providing support to the knee, low back, hip, shoulder, hamstring, and elbow in one design. The pre-cut sheet has a central anchoring portion (generally, 20), which may include a central hole 40 for allowing a joint to protrude. Projecting generally outwardly from the central anchoring portion 20 are fingers 30. As shown, the support article 10 may have separate upper and lower fingers terminating at upper ends 50A and lower ends 50B respectively. An alternative configuration of the body support is shown in FIG. 13. As illustrated, the article may be configured so that all fingers 30 extend in one direction away from the central anchoring portion 20.

The support article is an adhesive sheet having a skin-safe high tack adhesive on one side (not shown). The sheet has a high-stretch fabric base, which is preferably breathable. A stretch coefficient of approximately 140% is considered optimal, however a range of stretchability may be useful. Acceptable adhesives and base fabrics are considered to be within the knowledge of persons skilled in the art of bandage and body tape manufacturing and are not discussed here in detail.

Of note, the support article of the present invention is pre-cut and marked with indicators allowing positioning of the article on a body part of a user. Ideally, the article will also be packaged with simple instructions (not shown) for the user to apply the article. For instance, the instructions may indicate that, after adhering the central anchoring portion 20, the user should measure up from the central anchoring portion 5 inches and adhere the "A" marked 60A finger tips 50A at that location. The user should measure down from the central anchoring portion 4 inches and adhere the "B" marked 60B finger tips 50B at that location. These measurements are merely for illustration and must be selected to be appropriate to the particular application desired (i.e. particular body part to be supported) and may further be dependent on the size of the user. The distances to stretch govern the tension on the fingers, which support the body part. As shown in FIG. 13, the fingers may have individual markings 60, each corresponding to a different placement direction and desired end point, which would be detailed in the accompanying instructions (not shown). Note that in both the variations the central anchoring portion 20 is adhered without stretching, therefore it has no tension.

A body support system is illustrated in FIGS. 2-11 and 17. The main components of the system are the support article 110 and body landmark articles 150A, 150B. The body landmark articles 150A, 150B avoid the need to perform a measurement in order to adhere the support article. They assist in positioning the support article.

As with the basic body support described above, the body support article 110 shown in FIG. 2 has a central anchoring portion 120 (also shown in FIG. 2 as having cutaway 140 for joint protrusion), and fingers 130 extending outwardly from the central anchoring portion 120. The fingers 130 are marked with indicators (shown as being separate upper and lower indicators 180A and 180B, respectively). The indicators correspond to indicators 180A and 180B on landmark articles 150A and 150B shown in FIGS. 3 and 4. The body support article 110 has a release liner (not shown), which is preferably scored along line 125 at the upper and lower boundaries of the central anchoring portion 120. The score lines 125 allow the release liner to be separated to expose the central anchoring portion 120 separately from the release liner(s) along fingers 130, so that the portions may be adhered in sequence.

Figure 3:
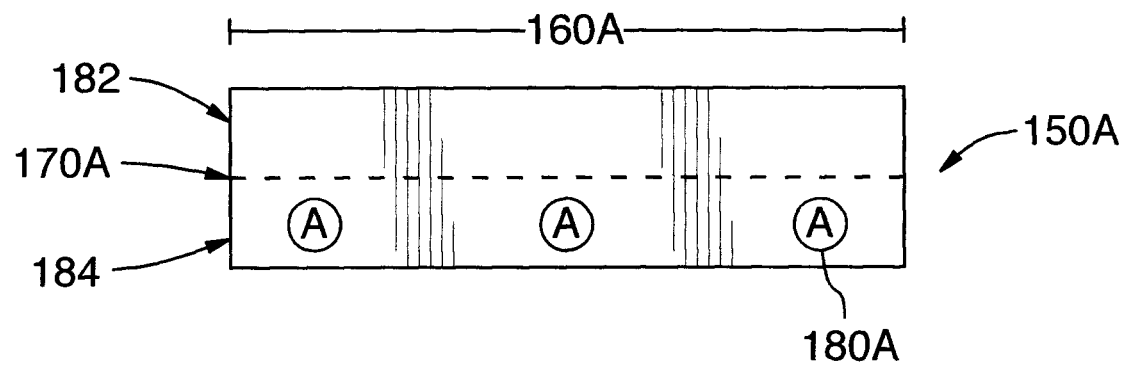
FIGS. 3 and 4 show top plan views of a body landmark article for use in the present invention (upper and lower, respectively).
Figure 4:
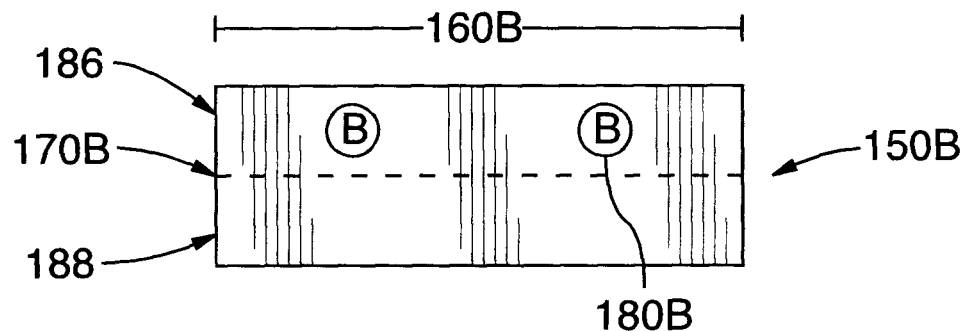

A preferred body landmark article design is shown in FIGS. 3 and 4. These correspond generally to a preferred design of upper and lower landmarks 150A, 150B (respectively). Each landmark article is preferably provided with a central fold line 170A, 170B (also scored on the release liner, not shown), which separates the landmark article into two halves (182, 184 on the upper landmark article and 186, 188 on the lower landmark article).

Figure 10:
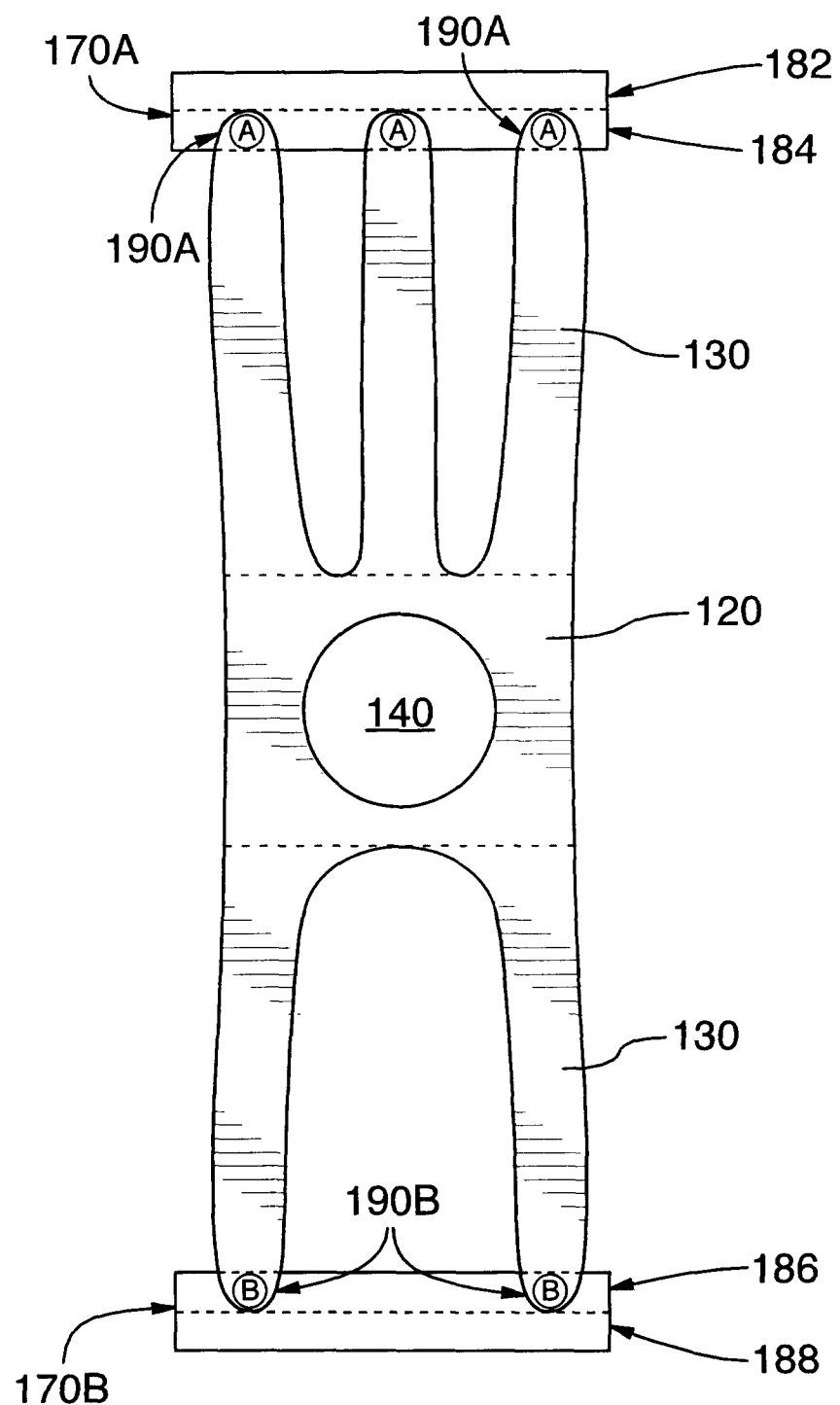
FIG. 10 shows a top plan view of completed installation of the body support system.

The installation process of the body support article 110 is illustrated in FIGS. 5 and 10. FIG. 5 illustrates the first phase of installation, while FIG. 10 illustrates the completed installation. To install the body support article 110, the release liner portion on the back of the central anchoring portion 120 is first removed along score lines 125. The central anchoring portion with adhesive exposed is then adhered (with zero tension, zero stretch) to the physiological centre that is desired to be supported. Cutaway 140 is used to center the anchor over an affected joint or other significant body feature (e.g. spine). At this point, the fingers 130 are at zero tension and are covered by the release liner. The pre-folded upper and lower body landmark articles 150A and 150B are then adhered at fold halves 182, 188 only. The length 160A, 160B of each of the upper and lower body landmark articles preferably corresponds to the distance away from the central anchoring portion that is needed for effective stretch support by the fingers. Therefore, before adhering the landmark articles, these may be used as rulers by positioning them extending outwardly lengthwise from the fold line 125, the end giving a visual guideline for where the landmark fold line 170A, 170B should then be positioned when the landmark article is situated in its installation position (shown in FIG. 5).

Once the halves 182, 188 are adhered so that the landmark articles are in their installation position, the release liners on the fingers 130 are removed and the fingers 130 are stretched so that they extend to the lines 170A, 170B. The upper fingers are stretched in accordance with their marked indicators to the marked positions on the landmark articles 150A, 150B (best shown in FIG. 10). The different lengths of the fingers 130 are pre-engineered so that different tensions will result when the fingers are stretched to lines 170A, 170B. Preferably, the tensions will range between about 10% to about 40% to support the affected area. Once the fingers 130 have been stretched and adhered in position, the landmark articles are unfolded. The release liner portions on the unadhered halves of the landmark articles are removed, exposing their adhesive layers. As shown in FIGS. 6 and 7, the folded half 184 is brought down to lie flat adjacent half 182 in the upper landmark article 150A. The folded half 186 is brought down to lie flat adjacent half 188 in the lower landmark article 150B. Thus, as shown in FIG. 10, the fingers 130 in completely stretched position are overlapped by the landmark articles 150A, 150B at 190A, 190B. This also serves to secure the ends of the fingers against peeling.

Figure 17:
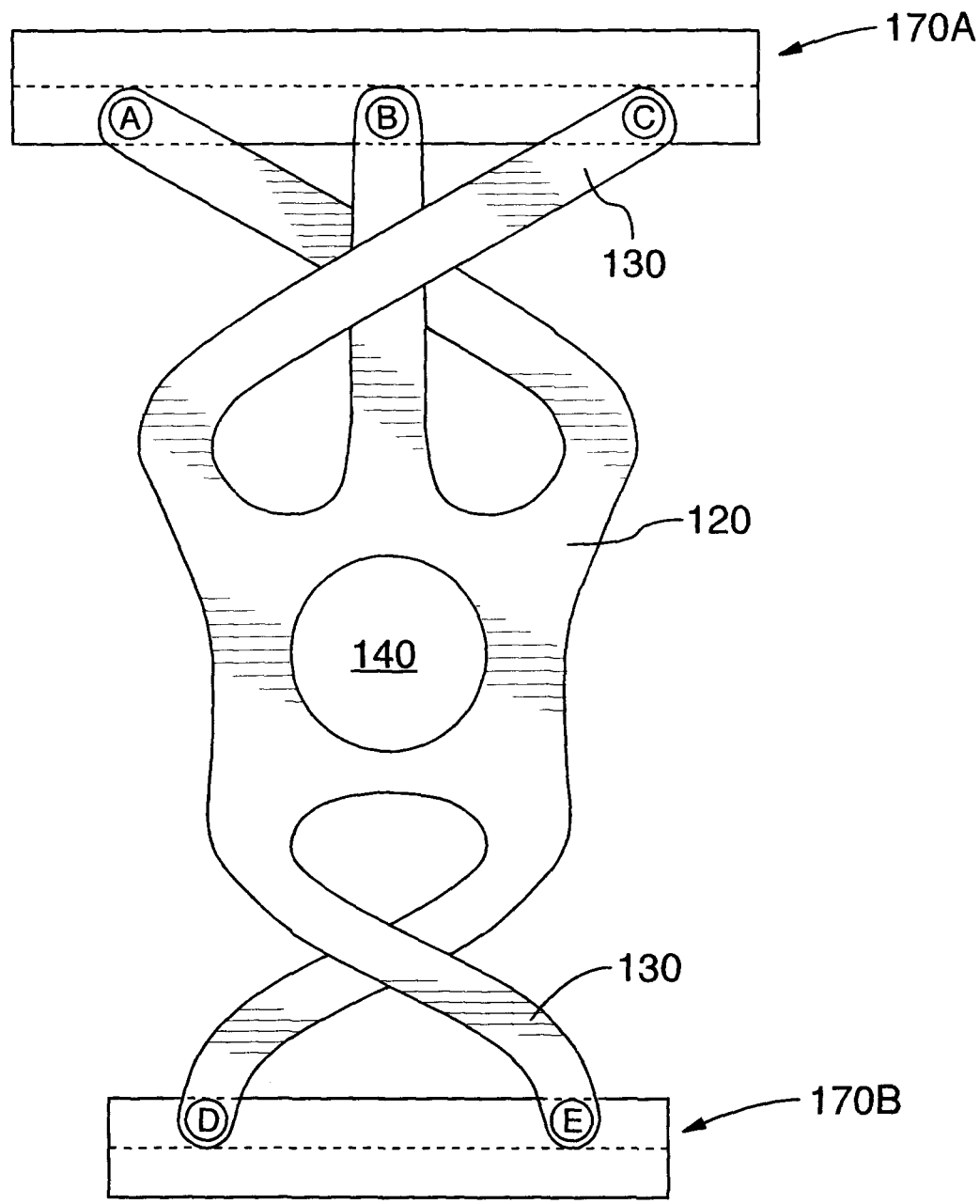
FIG. 17 shows a top plan view of a variation of the body support system shown in FIG. 10 marked with indicators for stretching the fingers in a cross-over pattern.

FIG. 17 shows an alternative variation of the embodiment shown in FIG. 10. In this variation, the fingers 130 and body landmark articles 170A, 170B are marked for application of the fingers in a cross-over pattern. The cross-over provides a higher concentration of positioning force focussed toward the center of the body part supported.

Figure 11:
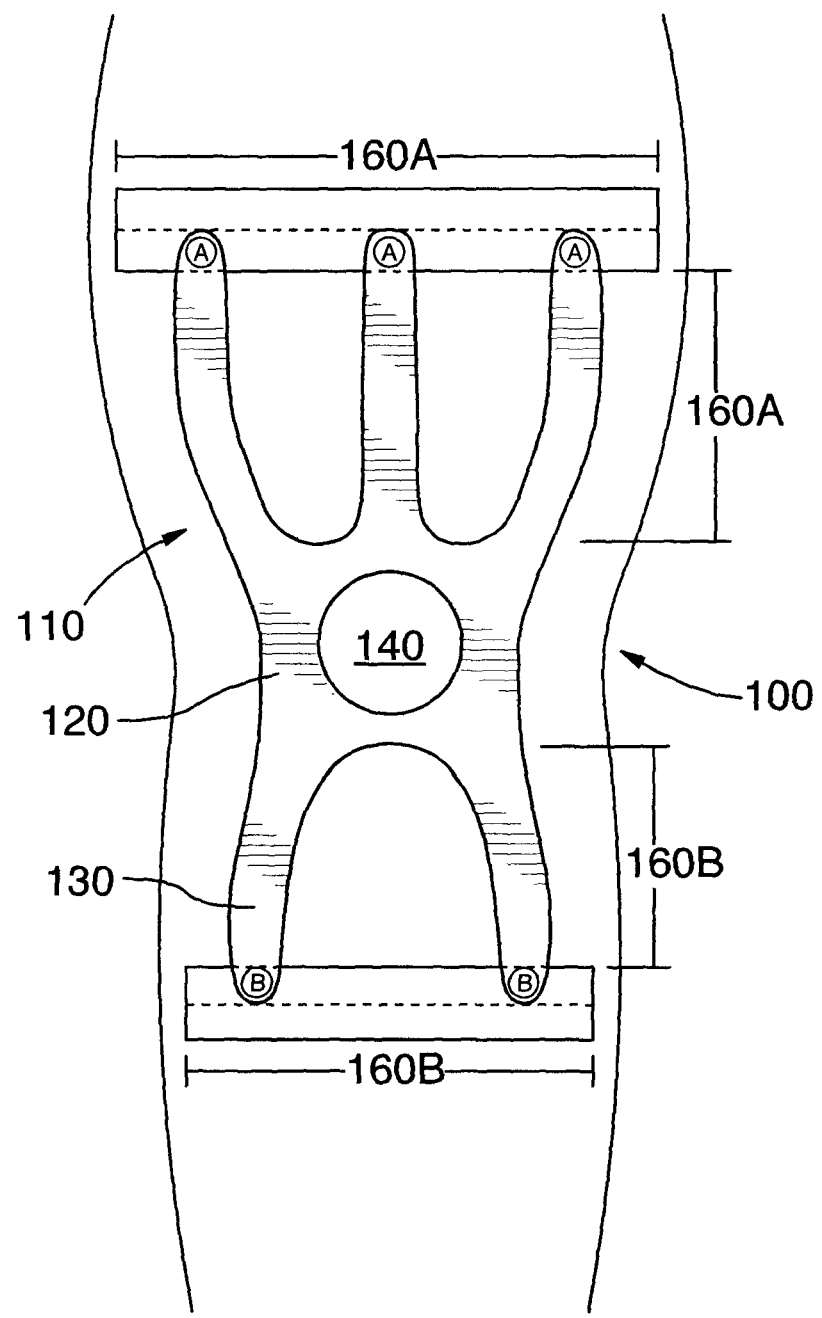
FIG. 11 shows a top plan view of completed installation of the body support system on a human body part.

FIG. 11 illustrates a sample placement of the body support article 110 on a human knee 100. As an illustration of the physiological effect of the support article, the use will be described having reference to the knee. It will be appreciated that the support article is equally capable of supporting another body part, either in the shape illustrated or in a similar shape having similar general features of a central anchoring portion and extensible fingers.

Patellofemoral pain syndrome is one of the most frequently experienced reasons for knee pain. Factors associated with patellofemoral pain syndrome are inactivation of the vastus medialus muscle, over-recruitment of the vastus lateralis, weakness of the rectus femoris and tibialis anterior. The patella ends up having excessive force pulling it laterally altering the normal wear and friction leading to pain and inflammation. Muscle weakness may attribute to arthrogenous inhibition, muscle fibre atrophy or myopathic change.

The support system provides adhesive support bracing objectively engineered, in the case of the knee, to control the position of the patella, altering the magnitude or distribution of patellofemoral joint pressures or stress on joint and soft tissue structures thus providing pain relief. The support system helps correct and realign movement of the patella to take pressure off inflamed tissue and alter "somatic" sensations thus increasing cutaneous proprioceptive acuity, quadriceps strength and neuromotor control.

A further effect is to provide facilitation to the regional muscles of the knee to influence the forces experienced by the knee (vastus medialis, rectus femoris, vastus lateralis, tibialis anterior). The support system further provides exteroceptive stimulation thus altering pain sensation and provides cutaneous proprioceptive input thus affecting muscle control.

These effects are achieved because of the differential tensions on the adhesive fingers pulled from the origin at the central anchoring portion. The pre-cut support article includes a central anatomically significant fixed point of origin and physiologically important projections to facilitate and inhibit muscles acting of the knee, governed by different levels of tension, in order to alter the forces over the knee in such a way as to reduce pain and improve range of motion.

Figure 12:
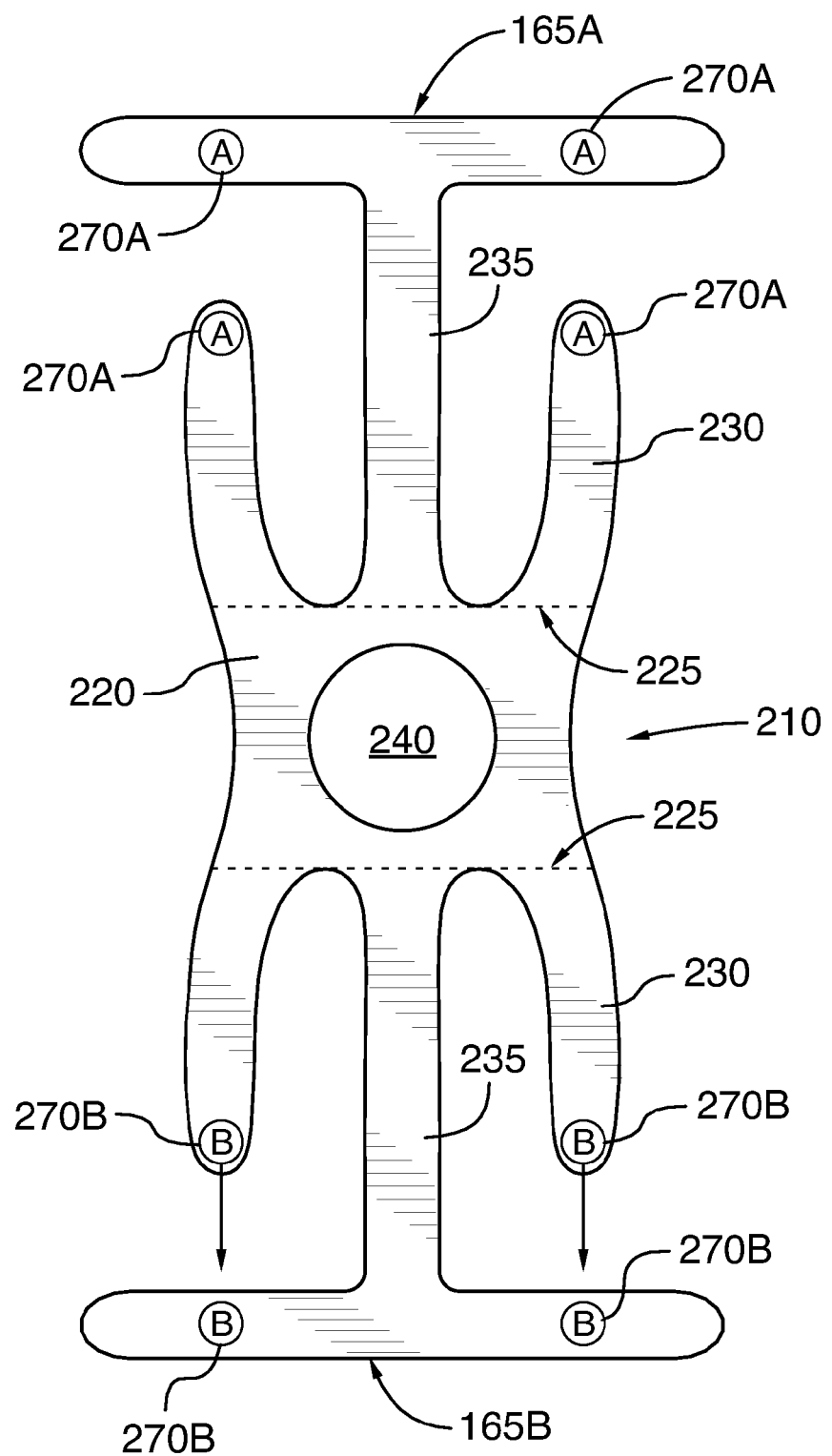
FIG. 12 shows a top plan view of a third body support article having integral upper and lower body landmarks.

A variant design is shown in FIG. 12. As illustrated, the body support article 210 may be provided as an integral piece with the landmark portions 165A, 165B. The article 210 has a central anchoring portion 220 with cutaway 240 and scored release liner lines 225. Fingers 230 project away from the central anchoring portion 220 and include marked indicators 270A, 270B. Also extending outwardly from the central anchoring portion is a pair of T-shaped landmark portions, each having trunk portion 235 and T portion 165A, 165B having laterally extending wings. The landmark portions are marked with indicators 270A, 270B corresponding to indicators on the fingers. Following installation and adhesion of the central anchoring portion 220, the landmark portions with their respective trunk portions are adhered (having zero tension) at their pre-measured distance away from the central anchoring portion. The fingers 230 are then stretched to match the indicators 270A, 270B together (respectively) to provide the pre-determined level of tension to support the body part.

Figure 14:
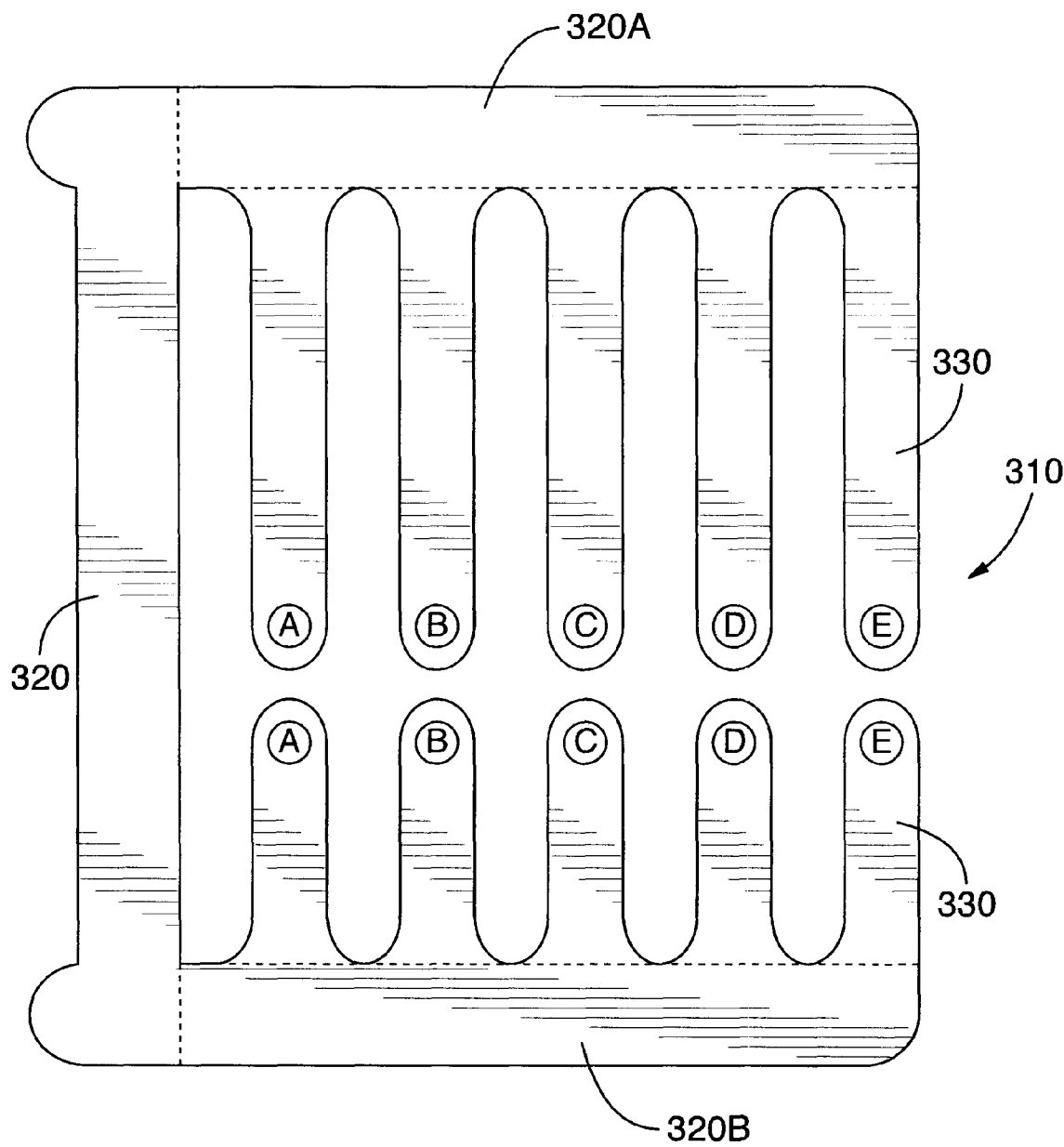
FIG. 14 shows a top plan view of a fourth body support article having a U-shaped central anchoring portion with fingers extending toward opposite sides of the U.
Figure 15:
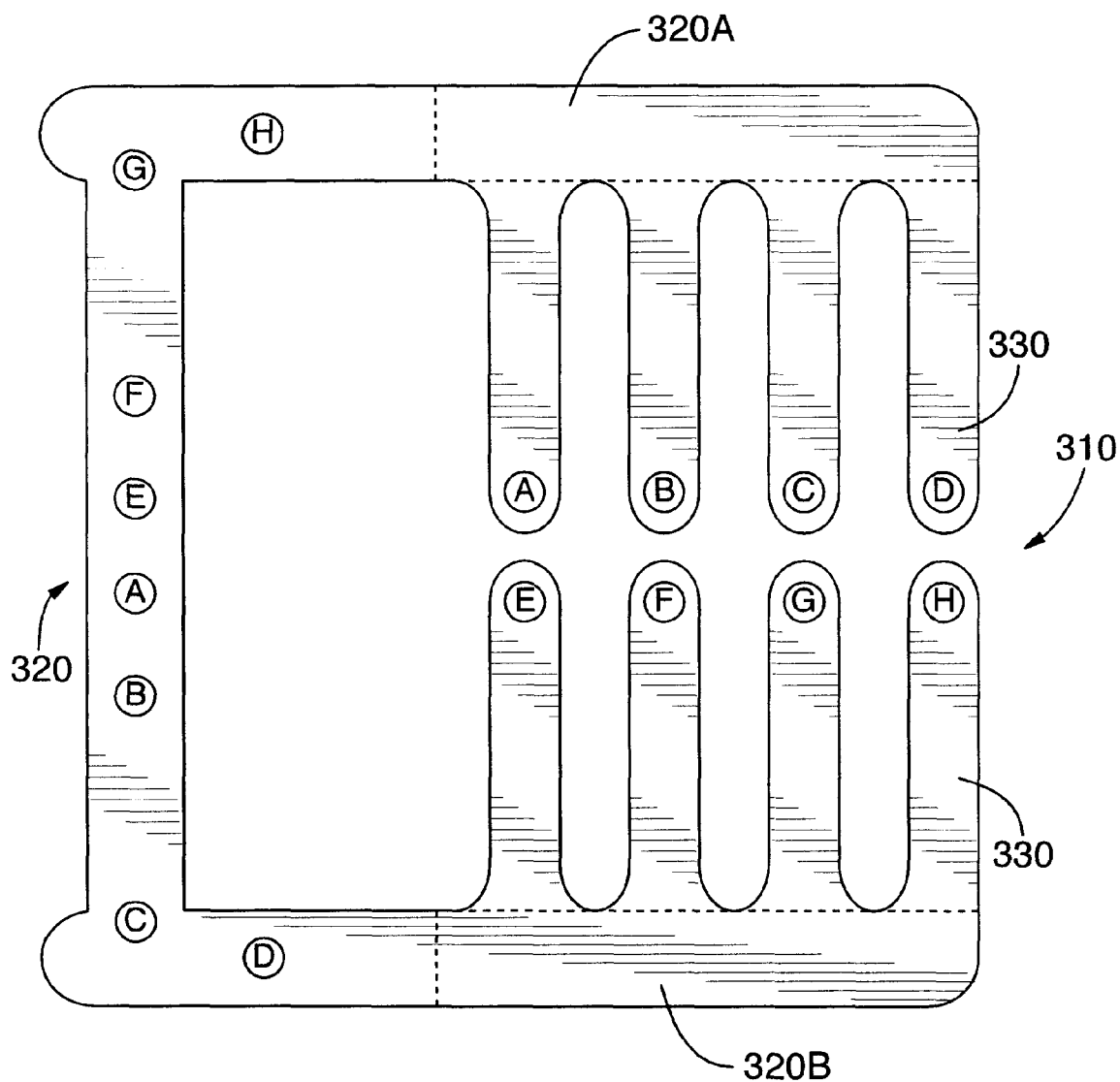
FIG. 15 shows a top plan view of a variation of the fourth body support article marked with indicators for stretching the fingers in an overlapping or interwoven pattern.
Figure 16:
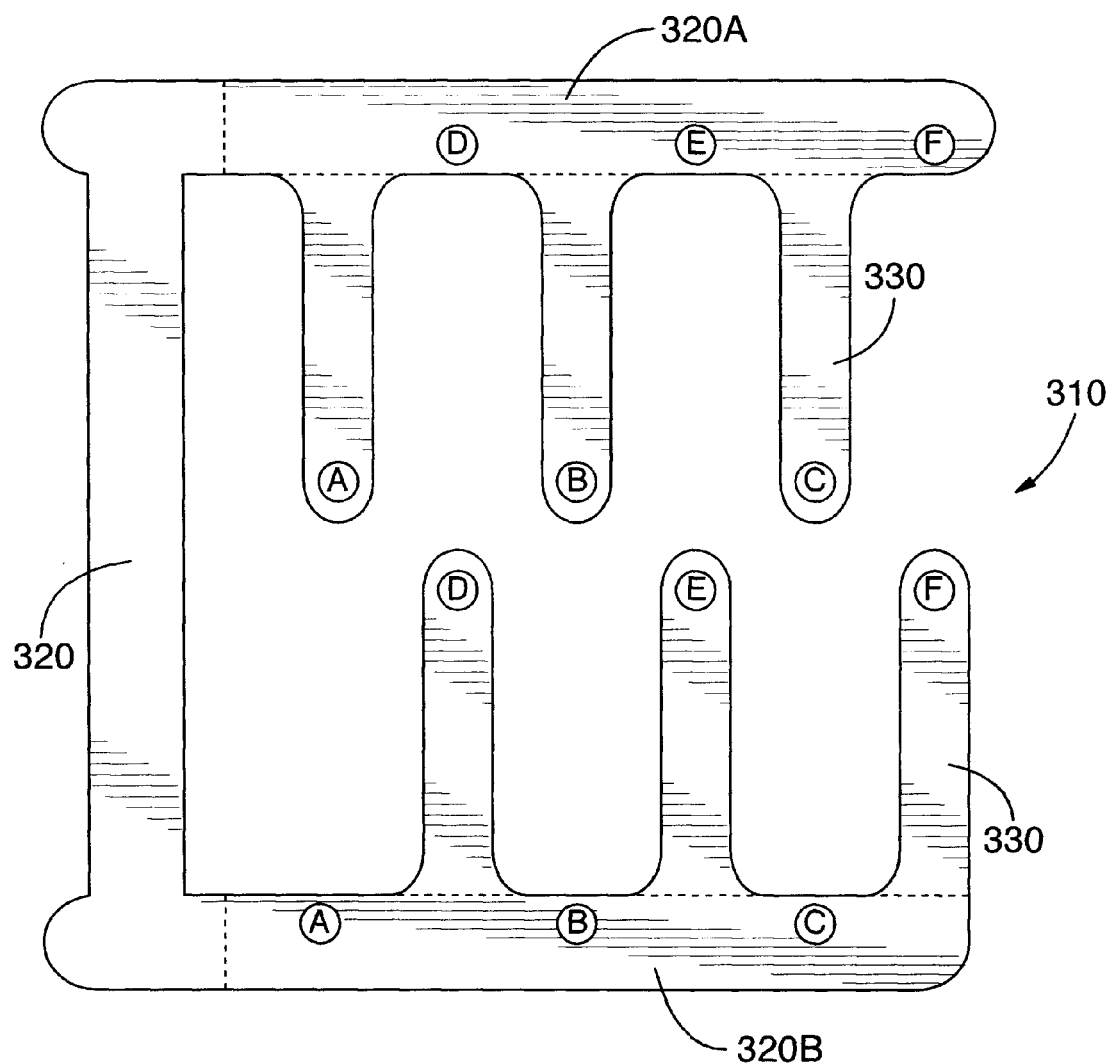
FIG. 16 shows a top plan view of a further variation of the fourth body support article marked with indicators for stretching the fingers in an interlaced or interdigitated pattern.

FIGS. 14-16 illustrate an alternative embodiment of a body support article 310 having a U-shaped central anchoring portion 320. Different marking configurations are possible, as shown in FIGS. 14-16. In FIG. 14, the fingers 330 (which extend from side portions 320A, 320B) are marked for application in a grid pattern. In FIG. 15, the fingers 330 are marked for application by stretching them to coordinating positions on the U-shaped central anchoring portion 320. The U-shaped central anchoring portion may thus take the place of the body landmark articles in the body support system embodiment described above. In FIG. 16, the fingers 330 are marked for application in an interlaced or interdigitated pattern (each finger being stretchable to extend to a corresponding indicator on the opposite side portion 320A, 320B).

The foregoing description illustrates only certain preferred embodiments of the invention. The invention is not limited to the foregoing examples. That is, persons skilled in the art will appreciate and understand that modifications and variations are, or will be, possible to utilize and carry out the teachings of the invention described herein. Accordingly, all suitable modifications, variations and equivalents may be resorted to, and such modifications, variations and equivalents are intended to fall within the scope of the invention as described and within the scope of the claims.

What is claimed is:

1. An adhesive support system, comprising:
an adhesive support article for supporting a body part of a user, comprising:
a single-sided high-stretch adhesive support tape blank precut into a sheet having a central anchoring portion and a plurality of fingers extending outwardly from the central anchoring portion; the sheet being marked with visual indicators to guide the user of the support article for:
applying the central anchoring portion onto a first exterior surface of the body part; and
stretching the fingers a predetermined distance away from the central anchoring portion according to the marked indicators and adhesively applying the fingers to a second exterior surface of the body part spaced away from the first exterior surface to support the body part by tethering the first and second exterior surfaces together without wrapping completely around the user's body at any point; and at least one adhesive body landmark article for adhering to an identifiable body landmark of the user to aid in gauging how far to stretch the fingers of the support article to adhere the fingers to the second exterior surface according to the marked indicators.

2. The adhesive support system of claim 1, wherein the body landmark article is marked with a second set of indicators corresponding to the indicators on the support article.

3. The adhesive support system of claim 1, wherein the system is packaged with instructions for application of the body landmark article before the support article.

4. The adhesive support system of claim 1, wherein the system is packaged with instructions for application of the body landmark article after the support article.

5. The adhesive support system of claim 1, wherein the body landmark article is pre-folded into halves at a central fold line and has a release liner scored at the central fold line to permit the pre-folded halves to be adhered separately.

6. The adhesive support system of claim 5, wherein at least one of the halves of the body landmark article is adapted to overlap and retain at least a portion of the fingers of the body support article when the fingers are adhered in the indicated position.

7. The adhesive support system of claim 6, wherein the overlapping half of the body landmark article is marked with indicators corresponding to indicators on the fingers that it overlaps.

\* \* \* \* \*